(12) United States Patent
Fan et al.

(10) Patent No.: US 7,352,933 B2
(45) Date of Patent: Apr. 1, 2008

(54) DIELECTRIC MICROCAVITY SENSORS

(75) Inventors: Xudong Fan, Austin, TX (US); Robert W. Wilson, Austin, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 130 days.

(21) Appl. No.: 10/855,462

(22) Filed: May 27, 2004

(65) Prior Publication Data

US 2005/0265658 A1  Dec. 1, 2005

(51) Int. Cl.
*G02B 6/42* (2006.01)
*G02B 6/00* (2006.01)

(52) U.S. Cl. .................. 385/43; 385/12; 385/27; 385/31; 385/39; 385/50

(58) Field of Classification Search .............. 385/12, 385/27, 31, 39, 43, 50
See application file for complete search history.

(56) References Cited

U.S. PATENT DOCUMENTS

| 3,833,284 | A | 9/1974 | Kaminow et al. |
|---|---|---|---|
| 4,715,672 | A | 12/1987 | Duguay et al. |
| 4,978,187 | A | 12/1990 | Minemura et al. |
| 5,077,822 | A | 12/1991 | Cremer |
| 6,389,197 | B1 | 5/2002 | Iltchenko et al. |
| 6,490,039 | B2 * | 12/2002 | Maleki et al. ............ 356/436 |
| 6,507,684 | B2 | 1/2003 | Tapalian et al. |
| 6,512,866 | B1 | 1/2003 | Fan et al. |
| 6,583,399 | B1 | 6/2003 | Hunziker et al. |
| 6,594,425 | B2 | 7/2003 | Tapalian et al. |
| 6,657,731 | B2 | 12/2003 | Tapalian et al. |
| 6,665,476 | B2 | 12/2003 | Braun et al. |
| 6,668,111 | B2 | 12/2003 | Tapalian et al. |
| 6,777,244 | B2 | 8/2004 | Pepper et al. |
| 6,781,696 | B1 | 8/2004 | Rosenberger et al. |
| 6,795,481 | B2 | 9/2004 | Maleki et al. |
| 6,853,479 | B1 | 2/2005 | Ilchenko et al. |
| 6,865,317 | B2 | 3/2005 | Vahala et al. |
| 6,879,752 | B1 | 4/2005 | Ilchenko et al. |
| 6,888,987 | B2 | 5/2005 | Sercel et al. |

(Continued)

FOREIGN PATENT DOCUMENTS

GB  2 293 883  4/1996

(Continued)

OTHER PUBLICATIONS

Blair et al., "Resonant-enhanced evanescent-wave fluorescence biosensing with cylindrical optical cavities", Applied Optics, vol. 40, No. 4, Feb. 1, 2001, pp. 570-582.

(Continued)

*Primary Examiner*—Frank G. Font
*Assistant Examiner*—Michael P. Mooney
(74) *Attorney, Agent, or Firm*—Robert S Moshrefzadeh

(57) ABSTRACT

The use of bulge-like microcavities in microcavity sensors provides advantages in alignment and reproducibility in manufacturing. Arrays of bulge-like microcavities may be used with multiple waveguides. In addition, the bulge-like microcavity may be formed with at least an outer layer made of a polymer material, and may be made entirely from polymer material. This facilitates manufacturing in that the microcavity may be molded, and may also be reproducibly molded in an array configuration.

10 Claims, 10 Drawing Sheets

U.S. PATENT DOCUMENTS

| | | | |
|---|---|---|---|
| 6,891,996 | B2 | 5/2005 | Sercel et al. |
| 6,891,997 | B2 | 5/2005 | Sercel et al. |
| 6,895,135 | B2 | 5/2005 | Kaneko et al. |
| 6,901,101 | B2 | 5/2005 | Frick |
| 7,091,049 | B2 | 8/2006 | Boga et al. |
| 2001/0038651 | A1 | 11/2001 | Maleki et al. |
| 2002/0018611 | A1 | 2/2002 | Maleki et al. |
| 2002/0041730 | A1 | 4/2002 | Sercel et al. |
| 2002/0044739 | A1* | 4/2002 | Vahala et al. ............. 385/30 |
| 2002/0068018 | A1 | 6/2002 | Pepper et al. |
| 2002/0079453 | A1 | 6/2002 | Tapalian et al. |
| 2002/0094150 | A1 | 7/2002 | Lim et al. |
| 2002/0097401 | A1 | 7/2002 | Maleki et al. |
| 2002/0172457 | A1 | 11/2002 | Tapalian et al. |
| 2002/0192680 | A1 | 12/2002 | Chan et al. |
| 2003/0016907 | A1 | 1/2003 | LoCasclo et al. |
| 2003/0082237 | A1 | 5/2003 | Cha et al. |
| 2004/0023396 | A1 | 2/2004 | Boyd et al. |
| 2004/0091212 | A1 | 5/2004 | Strecker et al. |
| 2004/0120638 | A1 | 6/2004 | Frick |
| 2004/0146431 | A1 | 7/2004 | Scherer et al. |
| 2004/0196465 | A1 | 10/2004 | Arnold et al. |
| 2005/0035278 | A1 | 2/2005 | Margalit et al. |
| 2005/0078731 | A1 | 4/2005 | Fan et al. |
| 2005/0105868 | A1 | 5/2005 | Arakida |
| 2005/0111309 | A1 | 5/2005 | Peng |
| 2005/0147372 | A1 | 7/2005 | Bourdelais et al. |
| 2005/0249509 | A1 | 11/2005 | Nagarajan et al. |
| 2006/0170931 | A1 | 8/2006 | Guo et al. |

FOREIGN PATENT DOCUMENTS

| | | |
|---|---|---|
| GB | 2 387 130 | 10/2003 |
| WO | WO 01/40757 A2 | 6/2001 |
| WO | WO 01/67565 | 9/2001 |
| WO | WO 01/85341 | 11/2001 |
| WO | WO 02/13337 | 2/2002 |
| WO | WO 02/13337 A1 * | 2/2002 |
| WO | WO 02/16986 | 2/2002 |
| WO | WO 2004/038370 A2 | 5/2004 |

OTHER PUBLICATIONS

Boyd et al., "Sensitive disk resonator photonic biosensor", Applied Optics, vol. 40, No. 31, Nov. 1, 2001, pp. 5742-5747.

Coffer et al., "Strategies Toward the Development of Integrated Chemical Sensors Fabricated from Light Emitting Porous Silicon", Proceedings of the SPIE, vol. 3226, 1997, pp. 168-179.

Crisan et al., "Sol-Gel Preparation of Thin Films for Integrated Optics", 10th International Symposium on Electron Devices for Microwave and Optoelectronic Applications, Nov. 18-19, 2002, Manchester, UK., pp. 205-210.

Krioukov et al., "Sensor based on an integrated optical microcavity", Optics Letters, vol. 27, No. 7, Apr. 1, 2002, pp. 512-514.

Luk, J.M.C., et al; "Rapid and Sensitive Detection of *Salmonella* (O : 6,7) by Immunomagnetic Monoclonal Antibody-Based Assays", *Journal of Immunological Methods* (1991); vol. 137; pp. 1-8.

Pettipher, G.L., et al; "Rapid Enumeration of Microorganisms in Foods by the Direct Epifluorescent Filter Technique", *Applied and Environmental Microbiology* (Oct. 1982); vol. 44, No. 4; pp. 809-813.

Pipino et al., "Evanescent wave cavity ring-down spectroscopy with a total-internal-reflection minicavity", Review of Scientific Instruments, American Institute of Physics, vol. 68, No. 8, Aug. 8, 1997, pp. 2978-2989.

Plowman, T.E., et al; "Femtomolar Sensitivity Using a Channel-Etched Thin Film Waveguide Fluoroimmunosensor", *Biosensors & Bioelectronics* (1996); Elsevier Science Ltd.; vol. 11, No. 1/2; pp. 149-160.

Popescu, A., et al; "The Gram Stain after More than a Century", *Biotechnic and Histochemistry* (1996); vol. 71, No. 3; pp. 145-151.

Shibata et al., "Laser Emission from Dye-Doped Organic-Inorganic Particles of Mircocavity Structure", Journal of Sol-Gel Science and Technology, vol. 8, 1997, pp. 959-964.

Tortorello, M.L., et al; "Antibody-Direct Epifluorescent Filter Technique for Rapid, Direct Enumeration of *Escherichia coli* O157:H7 in Beef", *Applied and Environmental Microbiology* (Oct. 1994); vol. 60, No. 10; pp. 3553-3559.

Tortorello, M.L., et al; "Rapid Identification of *Escherichia coli* O157:H7 in Bovine Feces Using the Antibody-Direct Epifluorescent Filter Technique (Ab-DEFT)", *Veterinary Microbiology* (1996); vol. 51; pp. 343-349.

Vernooy, D.W., et al; "High-Q Measurements of Fused-Silica Microspheres in the Near Infrared", *Optics Letters* (Feb. 15, 1998); vol. 23, No. 4; pp. 247-249.

Wark et al., "Incorporation of organic dye molecules in nanoporous crystals for the development of hexagonal solid state microlasers", Proceedings of the SPIE, vol. 4456, 2001, pp. 57-67.

Lu et al., "Chemical sensors based on hydrophobic porous sol-gel films and ATR-FTIR spectroscopy", Sensors and Actuators B, Elsevier Sequoia S.A., vol. B36, No. 1, 2, and 3, Oct. 1996, pp. 517-521.

Xu, G.; "Gram Stain", University of Pennsylvania Health System [on line]; [available on the internet on Oct. 31, 1997]; [retrieved from the internet on Dec. 15, 2004]; URL <http://www.uphs.upenn.edu/bugdrug/antibiotic_manual/gram.htm>; pp. 10.

Vollmer, F., et al; "Protein Detection by Optical Shift of a Resonant Microcavity", *Applied Physics Letters* (May 27, 2002); vol. 80, No. 21; pp. 4057-4059.

Armani, D.K., et al; "Ultra-High-Q Toroid Microcavity on a Chip", Letters to Nature, *Nature* (Feb. 27, 2003); vol. 421, Nature Publishing Group; pp. 925-928.

Tapalian, C., et al; "High-Q Silica Microsphere Optical Resonator Sensors Using Stripline-Pedestal Anti-Resonant Reflecting Optical Waveguide Couplers"; *Proceedings from SPIE, Photonics West 2003* (Jan. 25-31, 2003); vol. 4969; Laser Resonators and Beam Control VI; Item 4969-30; pp. 11-22.

Burlak, G., et al; "Electromagnetic Oscillations in a Multilayer Spherical Stack", *Optics Communications* (Jun. 1, 2000); vol. 180; pp. 49-58.

Laine, J.-P., et al; "Microsphere Resonator Mode Characterization by Pedestal Anti-Resonant Reflecting Waveguide Coupler", *IEEE Photonics Technology Letters* (Aug. 2000); vol. 12, No. 8; pp. 1004-1006.

Burlak, G., et al; "Electromagnetic Eigenoscillations and Fields in a Dielectric Microsphere with Multilayer Spherical Stack", *Optics Communications* (Jan. 1, 2001); vol. 187; pp. 91-105.

Chan, S., et al; "Nanoscale Silicon Microcavities for Biosensing", *Materials Science & Engineering C* (2001); vol. 15; pp. 277-282.

Laine, J.-P., et al; "Acceleration Sensor Based on High-Q Optical Microsphere Resonator and Pedestal Antiresonant Reflecting Waveguide Coupler", *Sensors and Actuators A* (2001); vol. 93; pp. 1-7.

Kakarantzas, G., et al; "Miniature All-Fiber Devices Based on $CO_2$ Laser Microstructuring of Tapered Fibers", *Optics Letters* (Aug. 1, 2001); vol. 26, No. 15; pp. 1137-1139.

Chan, S., et al; "Identification of Gram Negative Bacteria Using Nanoscale Silicon Microcavities", *Journal of American Chemical Society* (2001); vol. 123; pp. 11797-11798.

Spillane, S.M., et al; "Ultralow-Threshold Raman Laser Using a Spherical Dielectric Microcavity", *Nature* (Feb. 7, 2002); vol. 415; pp. 621-623.

Lugo, J.E., et al; "Porous Silicon Multilayer Structures: A Photonic Band Gap Analysis", *Journal of Applied Physics* (Apr. 15, 2002); vol. 91, No. 8; pp. 4966-4972.

Burlak, G., et al; "Transmittance and Resonance Tunneling of the Optical Fields in the Microspherical Metal-Dielectric Structures", *Optics Communications* (2002); vol. 206; pp. 27-37.

Krioukov, E., et al; "Integrated Optical Microcavities for Enhanced Evanescent-Wave Spectroscopy", *Optics Letters* (Sep. 1, 2002); vol. 27, No. 17; pp. 1504-1506.

Sumetsky, M., "Whispering-Gallery-Bottle Microcavities: the Three-Dimensional Etalon", *Optics Letters* (Jan. 1, 2004); vol. 29, No. 1; pp. 8-10.

Martin, A.L., et al; "Replica-Molded High-Q Polymer Microresonators", *Optics Letters* (Mar. 15, 2004); vol. 29, No. 6; pp. 533-535.

*Appl. Phys. Lett.*, vol. 23, No. 5, Sep. 1, 1973, pp. 237-239.

Suematsu, et al., "Fundamental Transverse Electric Field ($TE_0$) Mode Selection for Thin-Film Asymmetric Light Guides," *Appl. Phys. Lett.*, vol. 21, No. 6, Sep. 15, 1972, pp. 291-293.

Tien, P., et al., "Novel Metal-clad Optical Components and Method of Isolating High-Index Substrates for Forming Integrated Optical Circuits," *Appl. Phys. Lett.*, vol. 27, No. 4, Aug. 15, 1975, pp. 251-253.

Yoneyama et al., "Nonradiative Dielectric Waveguide Circuit Components" *International Journal of Infrared and Millimeter Waves*, vol. 4, No. 3, (1983), pp. 439-449.

Chan, S., et al. "Porous Silicon Microcavities for Biosensing Applications," *Physical Status Solid*, vol. 182, (2000) pp. 541-546.

De Stefano, L., et al., "Optical Sensing of Flammable Substances Using Porous Silicon Microcavities," *Materials Science and Engineering*, vol. 100, Jul. 25, 2003, pp. 271-274.

Mulloni, V., et al. "Porous Silicon Microcavities as Optical Chemical Sensors," *Applied Physics Letters*, vol. 76, No. 18, May 1, 2000, pp. 2523-2525.

Garmire, E., et al., "Propagation Losses in Metal-Film-Substrate Optical Waveguides," *Journal of Quantum Electronics*, vol. QE-8, No. 10, Oct. 1972, pp. 763-766.

Kaminow, I.P., et al., "Metal-Clad Optical Waveguides: Analytical and Experimental Study," *Applied Optics*, vol. 13, No. 2, Feb. 1974, pp. 396-405.

Otto, A., et al., "Modification of the Total Reflection Modes in a Dielectric Film by One Metal Boundary," *Optics Communications*, vol. 3, No. 4, Jun. 1971, pp. 254-258.

Reisinger, A., "Attenuation Properties of Optical Waveguides with a Metal Boundary", no date.

U.S. Application entitled "Hybrid Sphere-Waveguide Resonators", filed Oct. 14, 2003, having U.S. Appl. No. 10/685,049.

U.S. Application entitled "Dielectric Microcavity Fluorosensors Excited With a Broadband Light Source", having U.S. Appl. No. 10/854,911, no date.

Johnson, B.R.; "Theory of Morphology-Dependent Resonances: Shape Resonances and Width Formulas", *Journal Optical Society of America A* (Feb. 1993); vol. 10, No. 2; pp. 343-352.

Knight, J.C., et al; "Mapping Whispering-Gallery Modes in Microspheres with a Near-Field Probe", *Optics Letters* (Jul. 15, 1995); vol. 20, No. 14; pp. 1515-1517.

Little, B.E., et al; "Pedestal Antiresonant Reflecting Waveguides for Robust Coupling to Microsphere Resonators and for Microphotonic Circuits", *Optics Letters* (Jan. 1, 2000); vol. 25, No. 1; pp. 73-75.

\* cited by examiner

DIELECTRIC MICROCAVITY SENSORS

FIELD OF THE INVENTION

The invention is directed generally to optical devices, and more particularly to optical sensors that use microresonators.

BACKGROUND

Microspheres and disks as optical resonators are currently under intensive investigation for applications in biochemical sensing. While microspheres made of glass feature a very high Q-factor ($>10^6$), lack of an appropriate approach to mass-producing and aligning microsphere resonators has hindered their acceptance as viable products. Microdisks or microrings based on semiconductor wafers, on the other hand, are relatively easy to fabricate in a large quantity. Their positions with respect to waveguides can be adjusted using lithographic technologies such as dry/wet etching and layer deposition. The Q-factors of these resonators, however, are typically below $10^4$, due at least in part to the surface roughness and to material absorption.

Other approaches to forming microcavities include forming cylindrical cavities by slicing through an optical fiber. This allows for mass-production of ring resonators with higher attainable Q-factors and controlled dimensions at low cost. However, such cylindrical microresonators feature only two-dimensional light confinement, and the light can propagate freely along the direction perpendicular to the planar surface. Consequently, any misalignment between the waveguide and the cylindrical ring resonator leads to the light being coupled into the lossy modes of the microcavity, resulting in degradation in the light enhancement.

SUMMARY OF THE INVENTION

The present invention is directed to the use of bulge-like microcavities.

In particular, one embodiment of the invention is directed to a microresonator array device that comprises at least first and second optical waveguides spaced apart from each other. A first bulge-like microcavity member is formed with at least first and second bulge-like microcavities and extends across the first and second optical waveguides. The first bulge-like microcavity is positioned proximate the first optical waveguide so as to optically couple light between the first bulge-like microcavity and the first optical waveguide. The second bulge-like microcavity is positioned proximate the second optical waveguide so as to optically couple light between the second bulge-like microcavity and the second optical waveguide.

Another embodiment of the invention is directed to a bulge-like microcavity device that comprises a light source emitting output light and a first optical waveguide coupled to receive the output light from the light source. A first bulge-like microcavity is disposed proximate the first waveguide for optical coupling with the first optical waveguide. The bulge-like cavity has at least an outer layer formed of a polymer material and has a body elongated along a longitudinal axis. The bulge-like microcavity has a whispering gallery mode having a value of Q higher than 1000 for light coupled from the first optical waveguide, and the polymer material is substantially transparent at the wavelength of the output light.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1A:
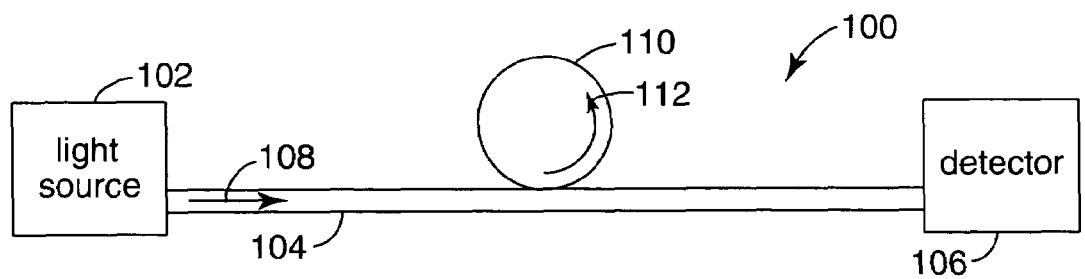
FIGS. 1A-1C schematically illustrate different embodiments of microcavity sensors.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is particularly applicable to optical sensors that use microcavity resonators. Such resonators may also be referred to as microresonators. The microresonators of the present invention can be readily reproduced, easily handled, can maintain a high cavity Q-factor and can be readily aligned to a coupling waveguide.

An example of a microcavity-waveguide system 100 that uses a microresonator is schematically illustrated in FIG. 1A. A light source 102 directs light along a waveguide 104 to a detector unit 106. The microresonator 110 is optically coupled to the waveguide 104. Light 108 from the light source 102 is launched into the waveguide 104 and propagates towards the detector unit 106. The microresonator 110 evanescently couples some of the light 108 out of the waveguide 104, the out-coupled light 112 propagating within the microresonator 110 at one of the resonant frequencies of the microresonator 110.

The light source 102 may be any suitable type of light source. For increased efficiency and sensitivity, it is advantageous that the light source produces light that is efficiently coupled into the waveguide 104, for example the light source may be a laser such as a laser diode. The light source 102 generates light 108 at a desired wavelength, or wavelength range. For example, where the microresonator is used in a sensor, the light source 102 generates light at a wavelength that interacts with the species being sensed. The species being sensed is typically located in proximity to the surface of the microresonator 110 so that the light propagating in the WGM interacts with the species being sensed. The light source 102 may also comprise a lamp, along with suitable optics for coupling light from the lamp into the waveguide 104.

For example, when the system 100 is used as a fluorosensor, the light propagating within the microresonator 110 is absorbed by a fluorescent molecule, such as a fluorescent dye, that is attached on the microresonator surface to an analyte or to a marker that indicates the presence of the analyte. In a more specific example, the surface of the microresonator may be attached with antibodies specific to a desired antigen analyte. The analyte antigen molecules, conjugated with a fluorescent dye, are introduced to the sensor system 100. The antigen molecules bind to the antibody molecules on the microresonator 110, thus holding the fluorescent dye molecules sufficiently close to the microresonator 110 that the light circulating within microresonator 110 evanescently couples to the fluorescent molecules. The absorbed light excites the fluorescent molecules and the molecules subsequently fluoresce at a wavelength different from the excitation wavelength. Detection of the fluorescent light confirms the presence of the analyte antigen.

In another example, the analyte antigen molecules are not conjugated with a fluorescent dye, but are allowed to bind to the antibodies attached to the microresonator surface. More antibodies, conjugated to fluorescent molecules, are subsequently introduced to the sensor, and bind to the antigen. Again, the fluorescent molecules are excited by an evanescent interaction with the light propagating within the microresonator 110, and detection of the subsequent fluorescence may be used to determine the presence and abundance of the analyte antigen.

The light source 102 may direct light into a number of different waveguides, of which the waveguide 104 is one example. The waveguide 104 may be any suitable type of waveguide and may be, for example, a planar waveguide or a channel waveguide formed in or on a substrate, such as a waveguide formed in a silica substrate. The waveguide 104 may also be an optical fiber.

The detector unit 106 includes a light detector, for example a photodiode or phototransistor, to detect light. The detector unit 106 may also include a wavelength sensitive device that selects the wavelength of light reaching the light detector. The wavelength selective device may be, for example, a filter, or a spectrometer. The wavelength selective device may be tunable so as to permit the user to actively change the wavelength of light incident on the light detector.

The microresonator 110 may be positioned in physical contact with, or very close to, the waveguide 104 so that a portion of the light 108 propagating along the waveguide 104 is evanescently coupled into the microresonator 110. The waveguide 104 typically has little or no cladding at the point where the microresonator 110 couples to the waveguide 104, so that the micro-resonator 110 couples directly to the core of the waveguide 104.

Figure 1B:
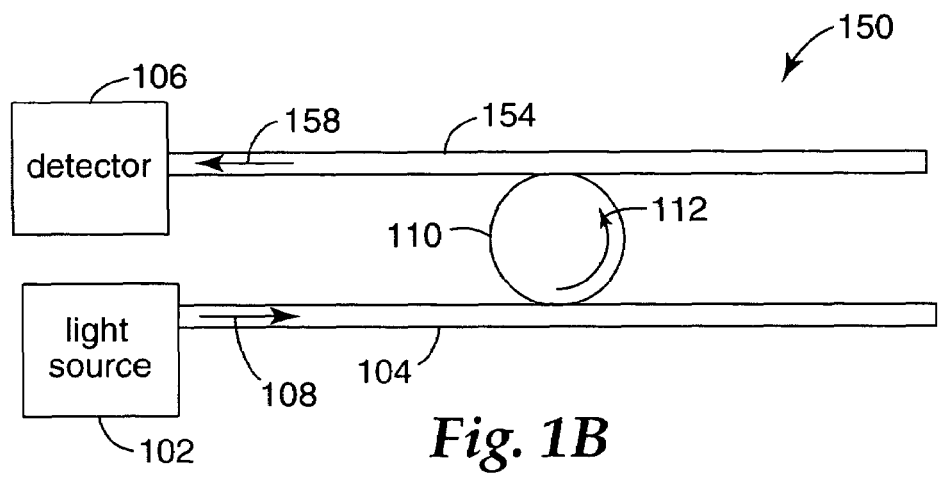

Another type of microresonator device 150 is schematically illustrated in FIG. 1B. In this device 150, light 158 from the microresonator 110 is coupled into a second waveguide 154, and propagates to the detector 106.

Figure 1C:
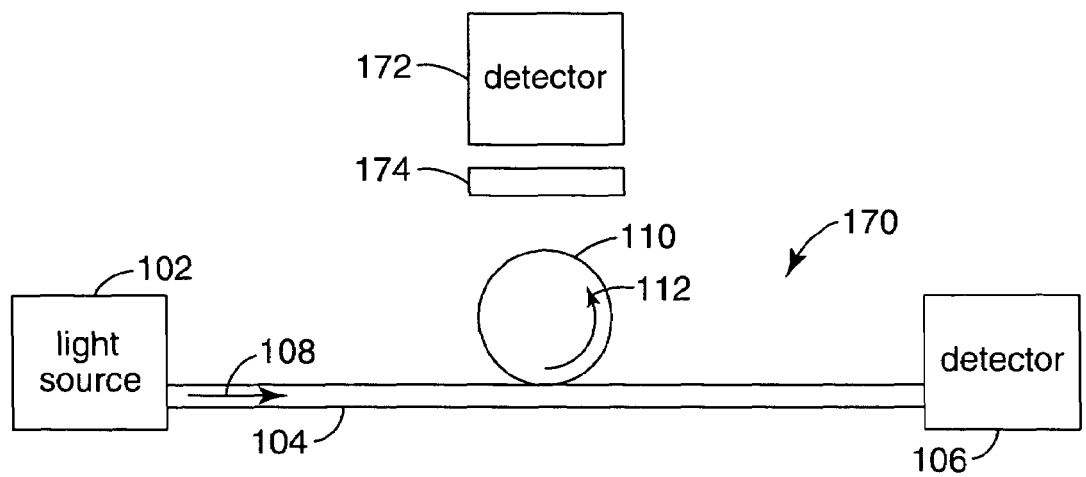

Another type of microresonator device 170 is schematically illustrated in FIG. 1C. In this device 170, a second detector 172 is positioned close to the microresonator 110 to detect light from the microresonator 110. The light detected by the second detector 172 does not pass to the second detector 172 via a waveguide, and is said to propagate through free space. The light from the microresonator 110 that is detected by the second detector 172 may be, for example, scattered out of the microresonator 110 or may be fluorescent light arising from excitation of a fluorescent species, attached to the surface of the microresonator, by light circulating within the microresonator 110. The second detector 172 may detect all wavelengths of light from the microresonator 110 or, for example through the use of a wavelength selective element 174 placed between the second detector 172 and the microresonator 110, may detect light that lies in a specific wavelength range. The wavelength selective element 174 may, for example, be a filter that rejects light at the excitation wavelength resonating within the microresonator 110 and that transmits light at the fluorescent wavelength. The second detector 172 may also be used with a configuration like that shown in FIG. 1B.

Figure 2:
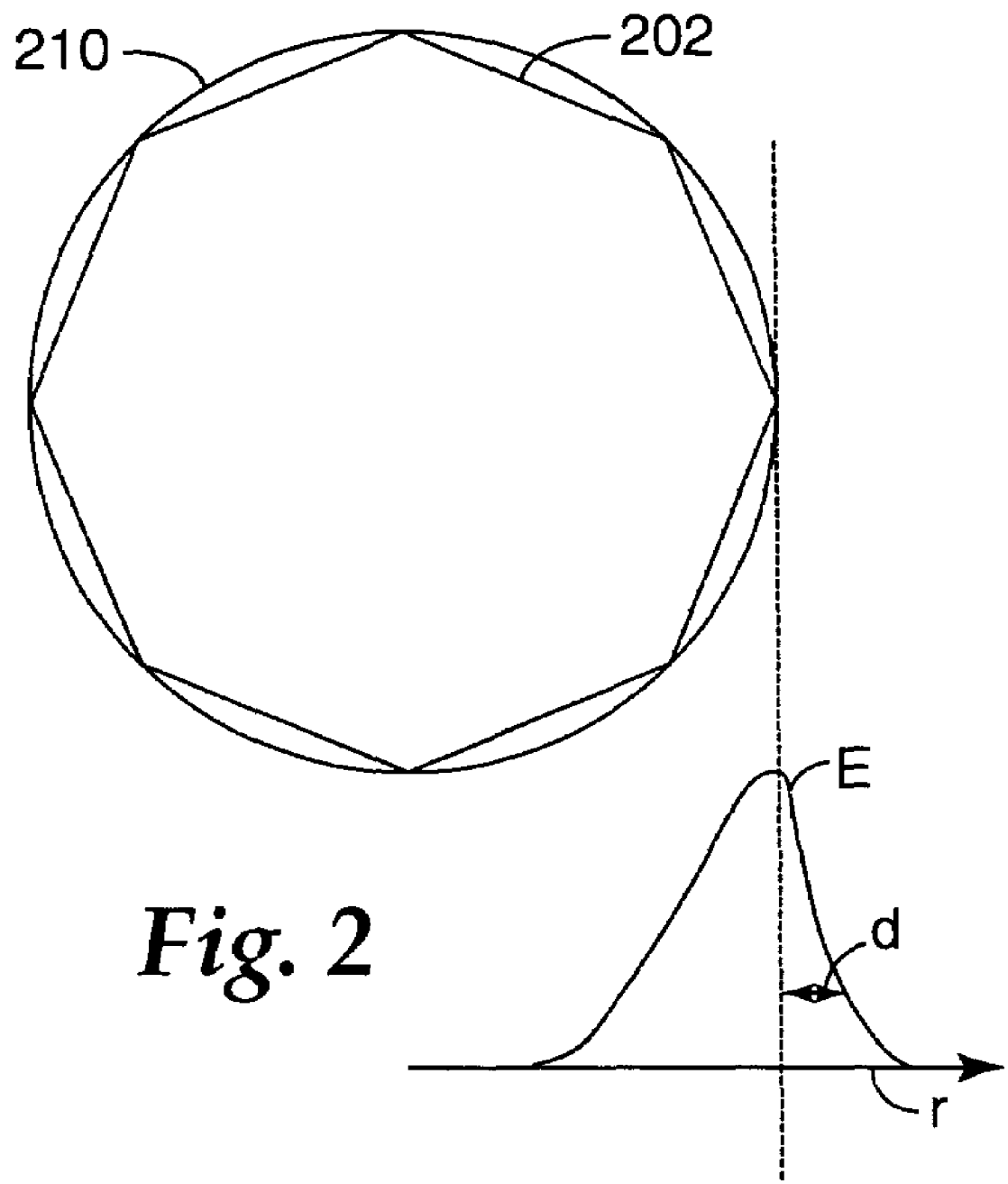
FIG. 2 schematically illustrates whispering gallery modes in a microcavity resonator.

Light propagates within the microresonator in so-called "whispering gallery modes", an example of which is schematically illustrated in FIG. 2. In a whispering gallery mode (WGM) 202, the light propagates around the micro-resonator 210 from an origin via a number of total internal reflections, until it returns to the origin. In the illustrated embodiment, the WGM 202 includes eight total internal reflections in a single round trip. It will be appreciated that the light may propagate within the micro-resonator 210 in other WGMs that correspond to different numbers of total internal reflections.

Furthermore, the WGM 202 only demonstrates a high Q-factor where the light is of such a wavelength that it constructively interferes after one round trip. Stated another way, the optical path length around the WGM 202 is equal to an integral number of wavelengths. This resonant condition for light in the planar WGM 202 illustrated in FIG. 2 can be stated mathematically as:

$$l\lambda_l = L \tag{1}$$

where $\lambda_l$ is the wavelength of the lth mode in vacuum, L is the optical length of one round trip of the WGM, and l is an integer, referred to as the mode number. Light from the waveguide 104 that satisfies the resonant condition (1) is efficiently coupled to the microresonator.

The electromagnetic field intensity of the WGM peaks at the interior surface of the microresonator 210. The electromagnetic field intensity of the WGM decays exponentially outside the microresonator 210, with a characteristic exponential decay length, d, given by $d \approx \lambda/n$ where $\lambda$ is the wavelength of the light in vacuum and n is the refractive index of the medium outside the microresonator 210. The field intensity, E, is schematically illustrated in FIG. 2 for the WGM 202 along the cross-section line AA'.

The microresonator 210 typically has a diameter in the range from 20 µm to a few millimeters, but is more often in the range 50 µm-500 µm. Furthermore, the waveguide is often tapered to increase the intensity of the optical field intensity outside the waveguide, thus increasing the amount of light that couples into the microresonator. In the case of an optical fiber waveguide, the fiber may be heated and tapered or etched to a total thickness of about 1-5 µm. Likewise, with a planar or channel waveguide, the waveguide thickness may be reduced at the region where the light is coupled to the microresonator. In addition to the waveguide being reduced in size, the thickness of the cladding around the waveguide may also be reduced. Various approaches to coupling the microresonator to a waveguide or fiber are discussed in greater detail in commonly owned and co-pending U.S. patent application Ser. No. 10/685,049, incorporated herein by reference.

Different types of microcavity resonators are now described with reference to FIGS. 3A-4C. Each of the WGMS 306, 316 and 326 shown in FIGS. 4A-4C corresponds to a WGM having only a single number of total internal reflections.

Figure 3A:
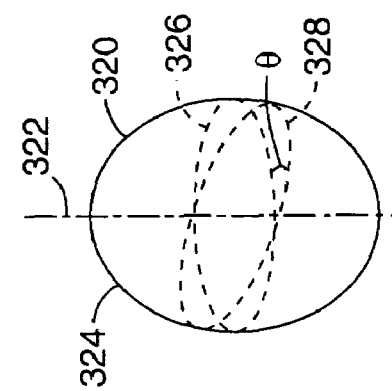
FIGS. 3A-3C schematically illustrate cylindrical, spherical and bulge-like microcavities respectively.

FIG. 3A schematically illustrates a cylindrical microresonator 300, with a longitudinal axis 302 that lies parallel to the circular walls 304 of the cylindrical microresonator 300. Such a microresonator may be formed, for example, using an optical fiber, where light is coupled tangentially into the side of the fiber, in a direction perpendicular to the fiber axis. The WGM 306 is shown in dashed lines, lying in a plane that is perpendicular to the axis 302. The cylindrical microresonator 300 does not support WGM modes that lie in a plane non-perpendicular to the axis, since such light does not follow a closed path and escapes from the resonant cavity.

Figure 4A:
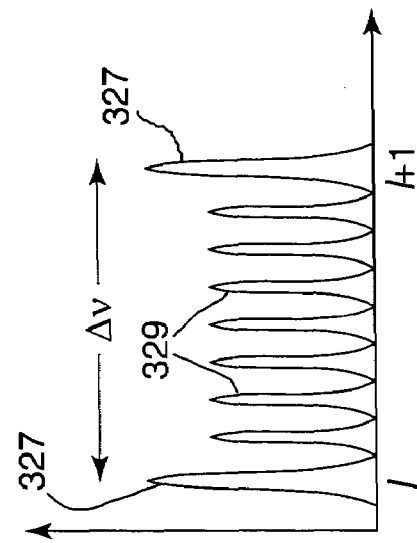
FIGS. 4A-4C schematically present portions of the resonant spectra of the microcavities illustrated in FIGS. 3A-3C respectively.

Accordingly, the resonant spectrum of the WGM 306 is like that shown in FIG. 4A, which shows the resonances plotted as a function of frequency, $v$. The lth resonant mode is separated from the (l+1)th resonant mode by a separation equal to $\Delta v$, also referred to as the free spectral range (FSR), where $\Delta v$ corresponds to an increase of one in the number of wavelengths around the WGM 306. The FSR may be calculated according to the following expression:

$$FSR = c/L \approx c/(\pi n D) \qquad (2)$$

where c is the speed of light in vacuum, n is the refractive index of the microcavity, D is the diameter of the microcavity and $\pi n D$ approximates the optical length of one round trip of the EWGM.

Note that FSR can also be expressed in terms of wavelength:

$$FSR(\text{in wavelength}) = \Delta v \lambda^2/c = \lambda^2/(\pi n D) \qquad (3)$$

where $\lambda$ is the light wavelength in vacuum. Both definitions of FSR can be used interchangeably.

Other EWGMs have different numbers of total internal reflections and, therefore, have optical path lengths different from that of the mode shown. The resonant frequencies associated with these other EGWMs are different from the resonant frequencies shown in FIG. 4A.

Figure 3B:
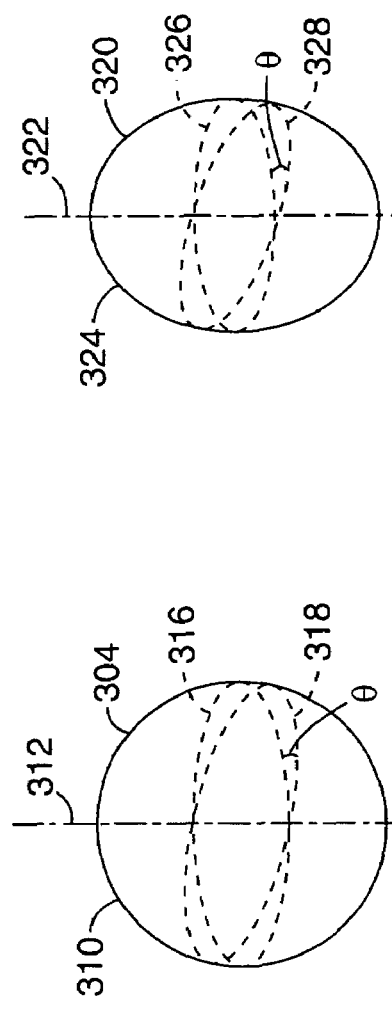

FIG. 3B schematically illustrates a spherical microresonator 310 positioned on an axis 312. Such a microresonator may be formed, for example, using a glass sphere having a spherical wall 314. The WGM 316 is shown, in dashed lines, lying in a plane perpendicular to the axis 312. The resonant spectrum of the WGM 316 is schematically illustrated in the graph shown in FIG. 4B. Like the WGM 306 of the cylindrical resonator, the frequency spacing between adjacent resonances is given by $\Delta v$ (the FSR), where $\Delta v$ corresponds to an increase of one in the number of whole integer wavelengths around the WGM 316. The FSR is given by expression (2) above, where D is the diameter of the spherical microresonator 310.

Unlike the cylindrical microresonator, however, the spherical microresonator 310 does support WGMs that do not lie perpendicular to the axis 312. One such WGM 318 is shown (in dashed lines) that lies at an angle, $\theta$, relative to the WGM 316. The WGM 316, lying perpendicular to the axis 312, is referred to as an equatorial mode and the WGM 318 is referred to as a non-equatorial, or azimuthal, mode. Since the microresonator 310 is spherical, however, the path length of the WGM 318 is identical to the path length of the WGM 316, and so the resonant frequencies for the WGM 318 are identical to those for WGM 316.

Figure 4B:
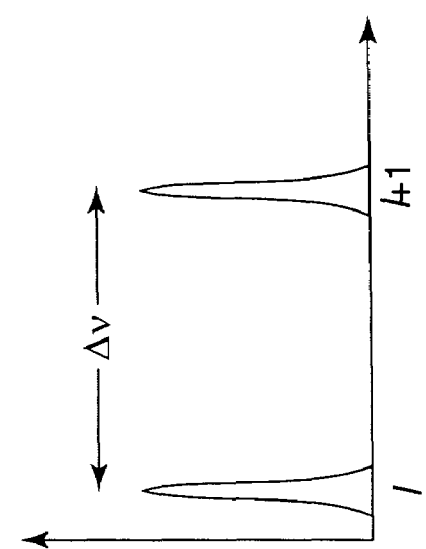

Other resonant spectra, corresponding to WGMs having different numbers of total internal reflections, may have resonances at different frequencies from those shown in FIG. 4B.

Figure 3C:
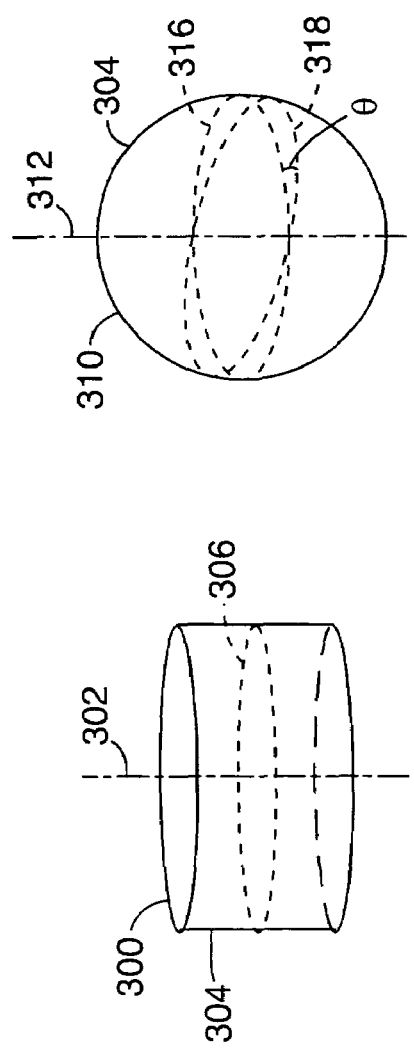

FIG. 3C schematically illustrates a microresonator 320 that is neither cylindrical, nor spherical. In the illustrated embodiment, the microresonator 320 has an ellipsoidal-like wall 324. The microresonator 320 is positioned on an axis 322. An equatorial WGM 326 is shown in dashed lines lying in a plane perpendicular to the axis 322. Some of the resonances of the equatorial WGM 326 are schematically shown as resonances 327 in the graph shown in FIG. 4C. The frequency spacing between adjacent resonances 327 of the WGM 326 is given by $\Delta v$ (the FSR), where $\Delta v$ corresponds to an increase of one in the number of whole integer wavelengths around the equatorial WGM 326. The FSR is given by expression (2) above, where $\pi n D$ approximates the optical length of one round trip of the EWGM.

Figure 4C:
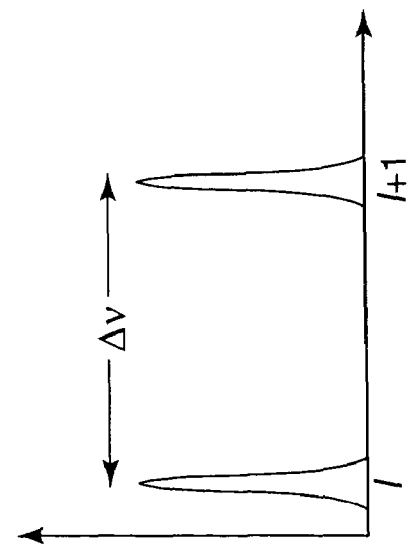

When the optical path of a mode is tilted through an angle, $\theta$, from zero, to form a non-equatorial path, the resonances associated with the non-equatorial path are not the same as those for the equatorial mode, however. This is because the path length around the elliptical microresonator varies when $\theta$ is increased from zero. In other words, the path length for the equatorial mode is different from that of the non-equatorial mode. Thus, different non-equatorial WGMs have different resonant frequencies that vary with values of $\theta$. Thus, the resonance spectrum for the microresonator 320 contains many resonances 329 for non-equatorial modes that "fit-in" to the regions between resonances 327 of the equatorial modes. Note that only a few of the non-equatorial resonances have been included in FIG. 4C, and the representation of non-equatorial resonances 329 in FIG. 4C is given only for qualitative purposes. The magnitudes of the non-equatorial resonances 329 are shown in FIG. 4C to be less than the magnitudes of the equatorial resonances 327 for purposes of distinguishing between equatorial and non-equatorial resonances. There is no intention, however, to indicate that the non-equatorial resonances 329 have a different Q-factor from the equatorial resonances 327.

Figure 5A:
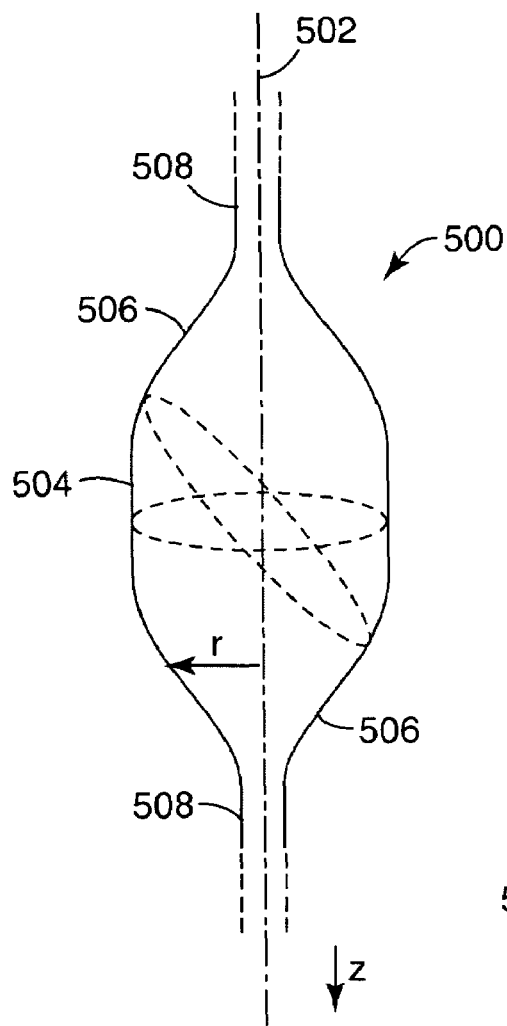
FIGS. 5A and 5B schematically illustrate different embodiments of bulge-like cavities, according to principles of the present invention.
Figure 5B:
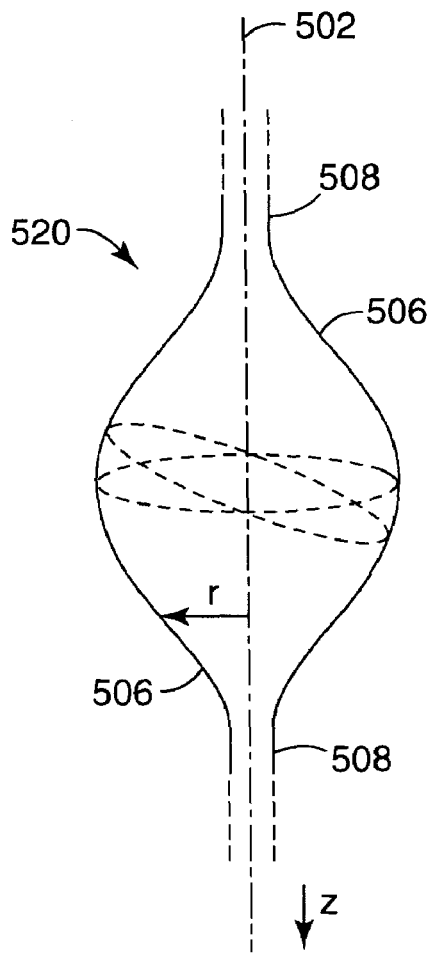

Many different shapes of microresonator cavity may be used to produce non-equatorial modes, of which two particular examples are provided in FIGS. 5A and 5B. In FIG. 5A, the microresonator 500 is formed about an axis 502. The microresonator 500 has a cylindrical region 504 with parallel walls and tapered regions 506 on either side of the cylindrical region 504. The tapered regions 506 may lead to necks 508 that have parallel walls that are narrower than the maximum width of the microresonator 500. The length of the cylindrical region 504 may be any suitable length, for example, in the range of 0 to 100 µm.

When the length of the cylindrical region 504 is zero, the microresonator 520 has a shape as is schematically illustrated in FIG. 5B. The profile of the tapered regions 506 may be selected as desired: the physical profiles of the tapered regions 506 and the length of the cylindrical region 504 affect the resonant spectrum for the microcavity. These microresonators 500 and 520, in which the radius, r, of the microresonator, measured from the longitudinal axis reaches a maximum value for one or more values of positions along the axis, in the z-direction, but where the profile is non-spherical and non-cylindrical, provide a resonant spectrum that is rich in non-equatorial modes.

For stable non-equatorial resonant modes, the radius, r, shows a maximum value in the microresonator, which helps to trap light in the non-equatorial modes, thus maintaining high values of Q. If the radius, r, shows a minimum value in the microresonator, light can escape from the microresonator more quickly, and so the value of Q is lower. Microresonator cavities that are non-spherical and non-cylindrical, and that exhibit a maximum value of r are referred to hereafter as bulge-like microresonator cavities.

Bulge-like microresonator cavities may be fabricated using various different methods. One approach is to form a bulge-like cavity member from a glass fiber. Sections of the glass fiber are heated, for example using a carbon dioxide laser, and stretched to form a necked region. In a particular example of this method, a length of Corning SMF28 optical communication fiber was treated by removing the protective covering along the length of the fiber where the bulge-like cavities were to be made. This exposed the fiber cladding which had a diameter of 125 µm. The exposed section of fiber was stretched between two translation stages, which were caused to move in opposition so as to maintain a relatively constant tension on the fiber. The tension on the fiber was monitored using a strain gauge. The output from a 50 W carbon dioxide laser was focused through a lens onto a short section of fiber. The lens was also mounted on a translation stage so as to be movable along the length of the fiber.

The laser caused the glass fiber to soften at the point where the beam was focused. The tension applied to the fiber caused the fiber to stretch at the softened region, thus reducing its diameter. To form a single taper the laser beam was scanned back and forth over a 0.3 mm distance at a rate of 2.4 mm/sec. The fiber was stretched at a rate of 0.01 mm/sec until its length increased by 10 mm. During this process the power from the laser was controlled to maintain a preset tension on the fiber of 0.2 g.

A second taper was produced using the same method at a point 10 mm along the fiber so as to form a bulge-like cavity between the two tapers. The process was then repeated to form a string of bulge-like cavities in the fiber. The tapered regions had a diameter of approximately 30 µm, while the diameter of the bulge-like cavity was about 125 µm.

Figure 6:
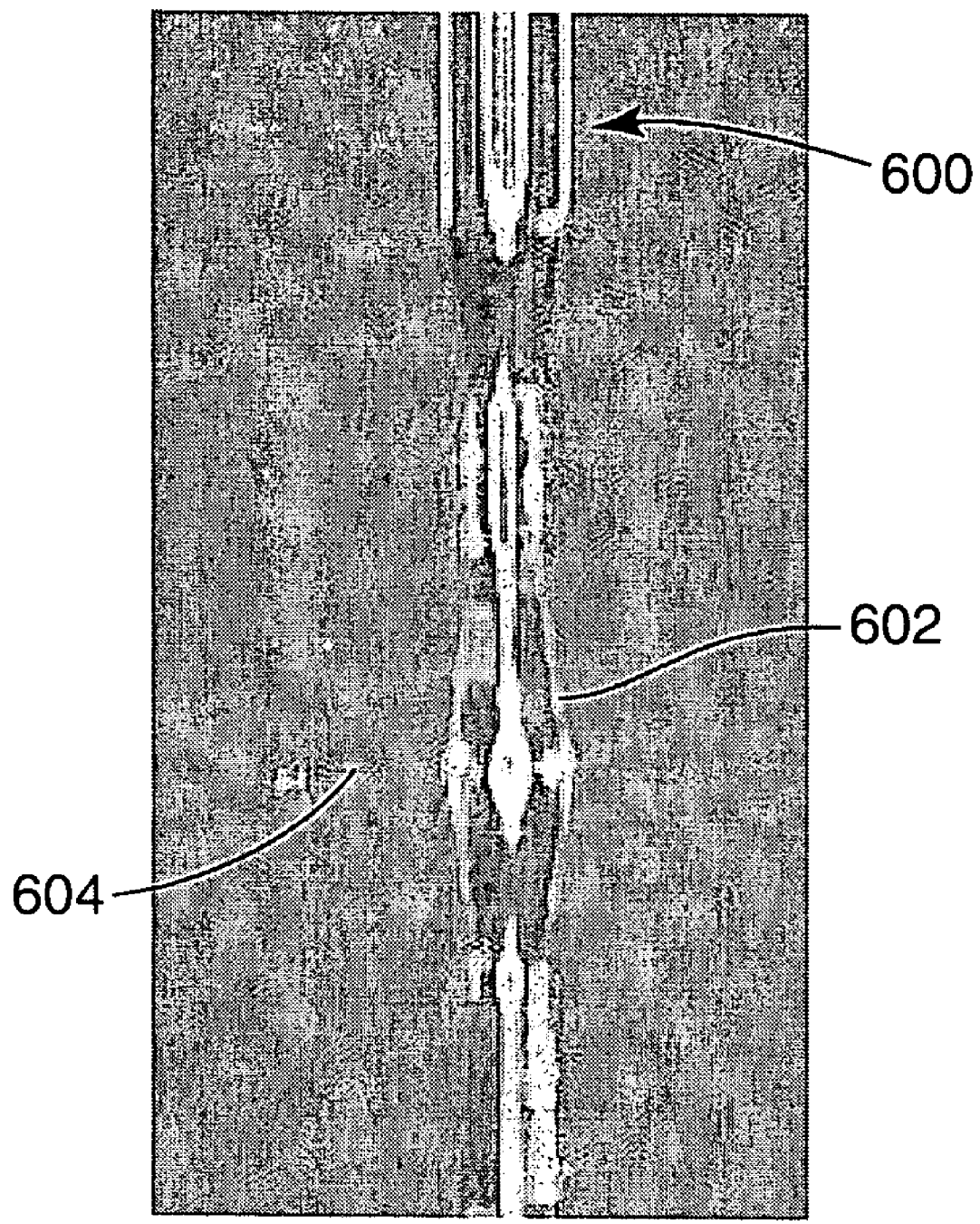
FIG. 6 shows a photograph of a bulge-like microcavity formed from an optical fiber.

The resulting bulge-like cavity can be characterized in the following manner. Light from a tunable diode laser was launched into an optical fiber that was tapered. The light was coupled from the fiber taper into the bulge-like cavity from the fiber taper. The experimental arrangement is illustrated in FIG. 6, which shows the SFM28 fiber 600 formed with a bulge-like cavity 602. The line 604 shows the path of the fiber taper used to couple light into the bulge-like cavity 602.

Figure 7:
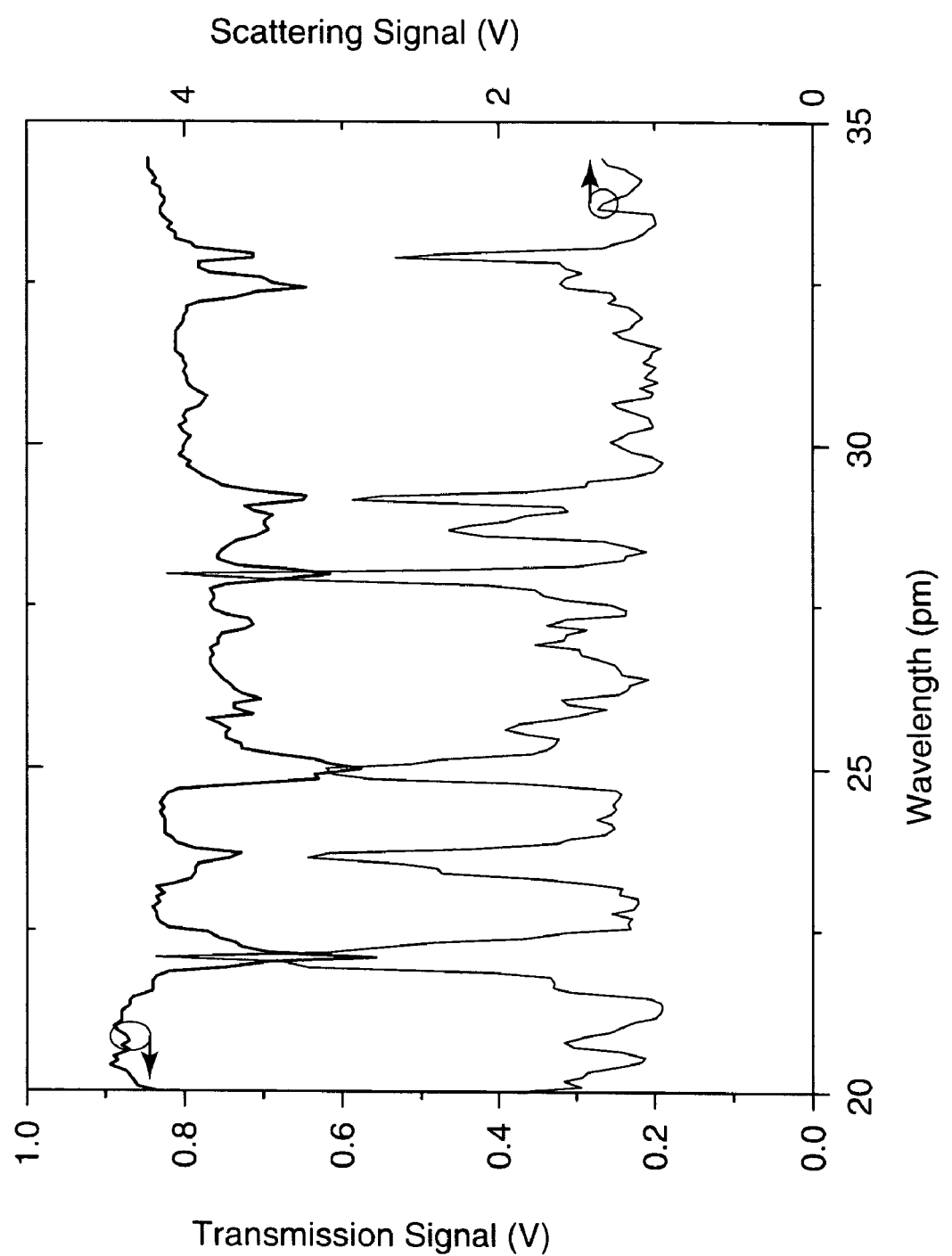
FIGS. 7, 8A and 8B present resonant spectra of the bulge-like cavity shown in FIG. 6.

One detector was used to monitor the light transmitted along the fiber taper, past the fiber taper and the bulge-like cavity, in a manner similar to the detector 106, illustrated in FIG. 1C. A second detector was positioned to measure light scattered out of the bulge-like cavity, in a position like that illustrated in FIG. 1C for the second detector 172. FIG. 7 shows the transmission spectrum (upper line) and scattering spectrum (lower line) generated when the laser was scanned over a spectral range of 15 pm with high spectral resolution. The highest Q-factor obtained is approximately $3.4 \times 10^6$.

Figure 8A:
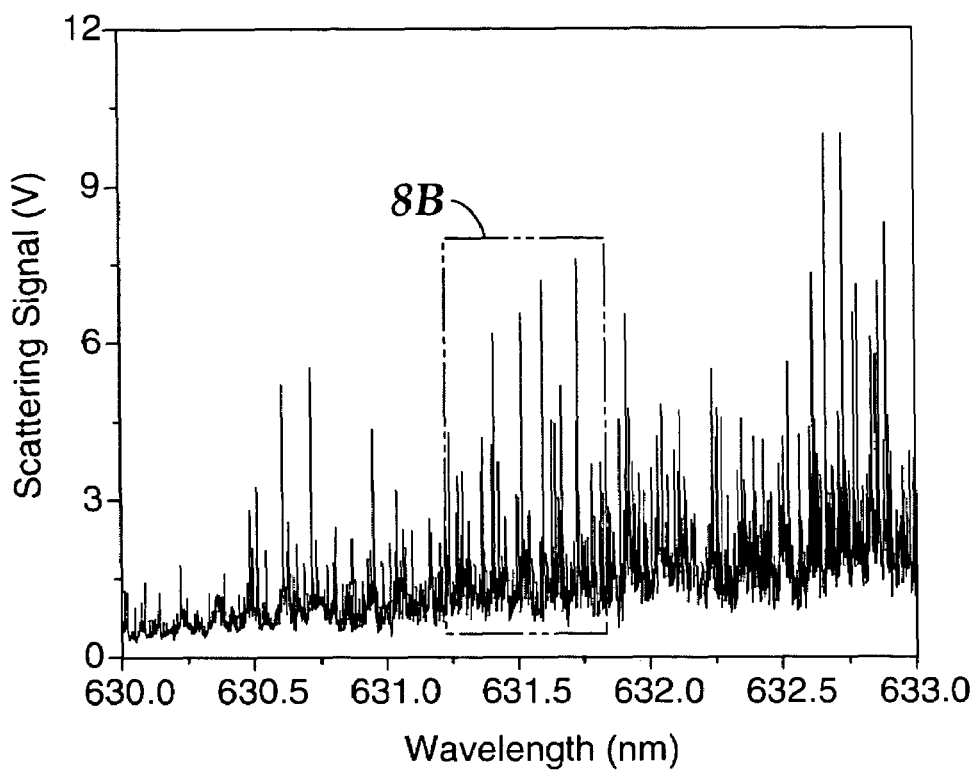
Figure 8B:
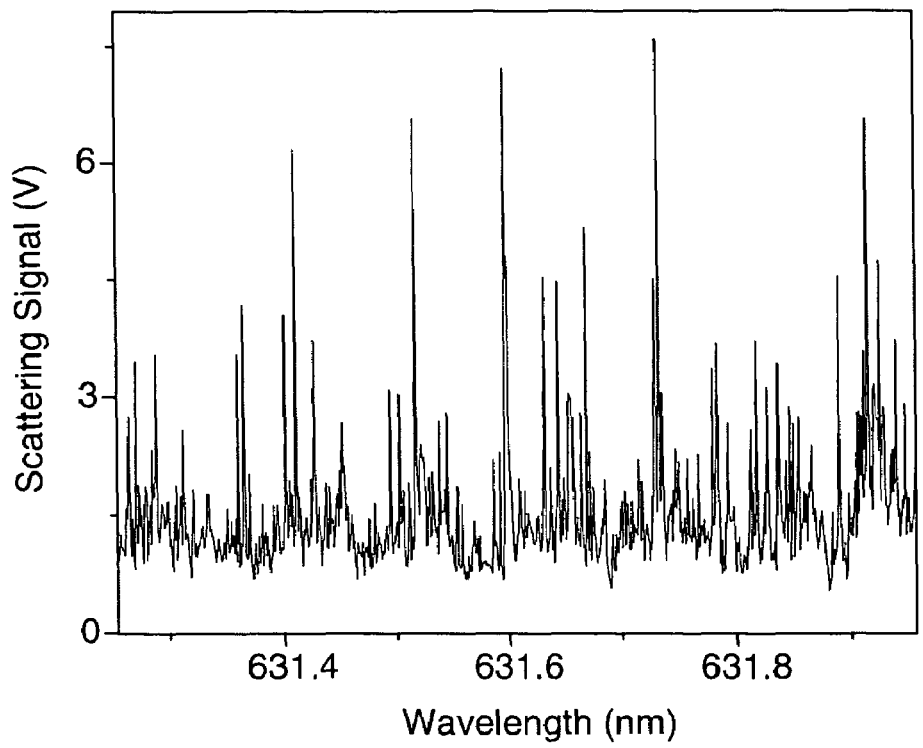

FIG. 8A shows the scattering spectrum on a larger spectral scale, over the range 630 nm-633 nm and FIG. 8B shows the scattering spectrum over a smaller range, 631.2 nm-632.0 nm. The bulge-like cavity supports many non-equatorial modes.

Figure 9A:
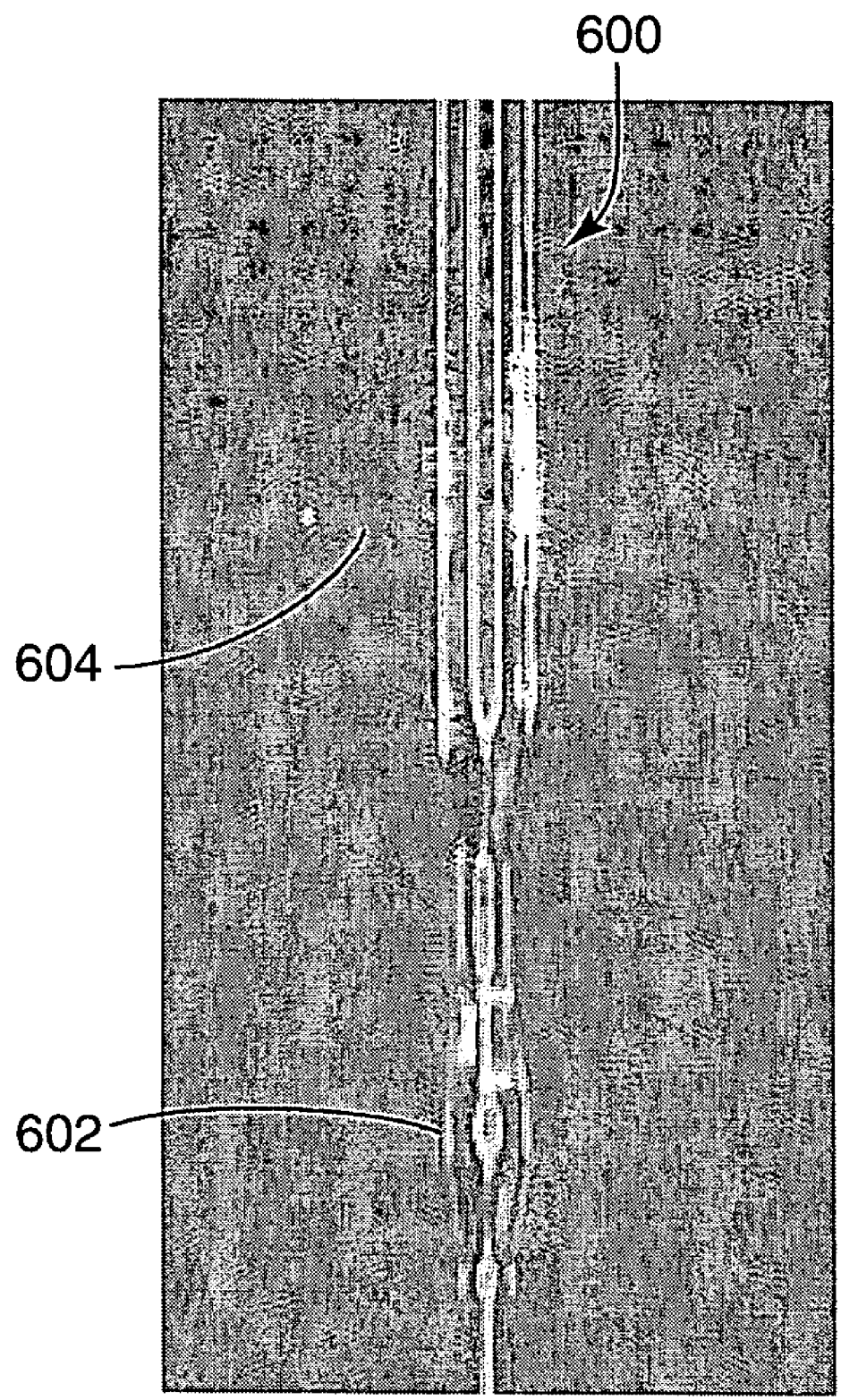
FIG. 9A shows a photograph of a cylindrical microcavity formed in an optical fiber.
Figure 9B:
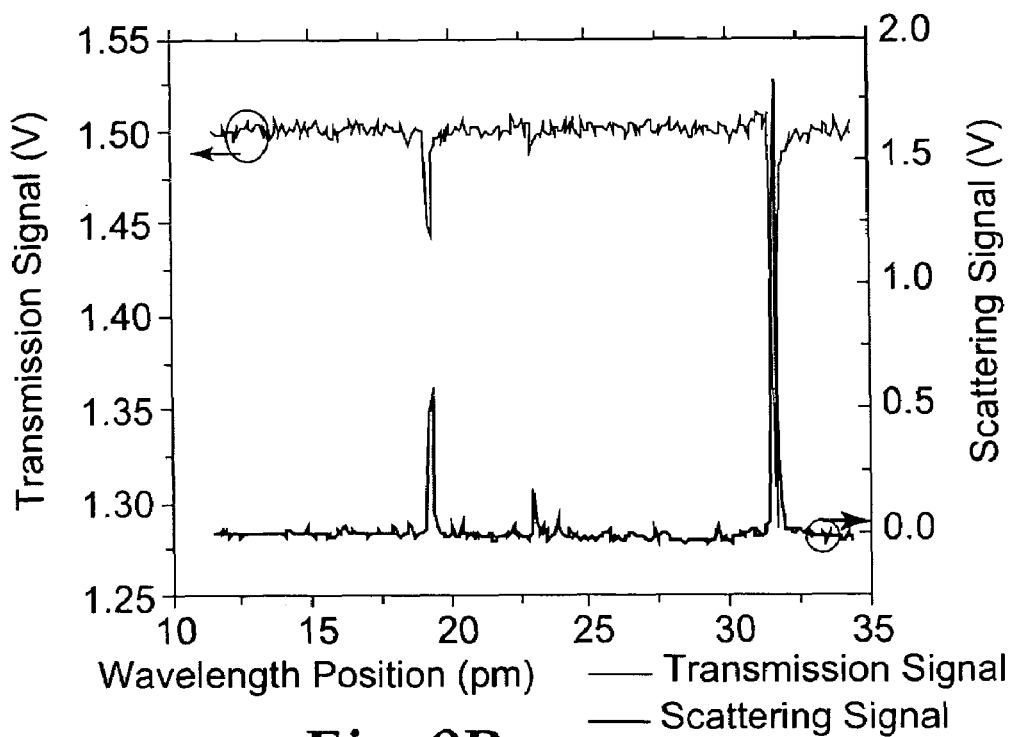
FIGS. 9B and 9C present resonant spectra of the cylindrical microcavity shown in FIG. 9A.

For a comparison, the mode structure of a cylindrical microresonator is also characterized. The cylindrical resonator was obtained by moving the SFM28 fiber so that a cylindrical portion of the fiber coupled to the tapered fiber coupler, as shown in FIG. 9A. FIG. 9B shows the transmission and scattering spectra for the cylindrical microresonator over a range of 25 pm. For comparison, the bulge-like cavity shows many more resonances within a comparable wavelength range, as shown in FIG. 7.

Figure 9C:
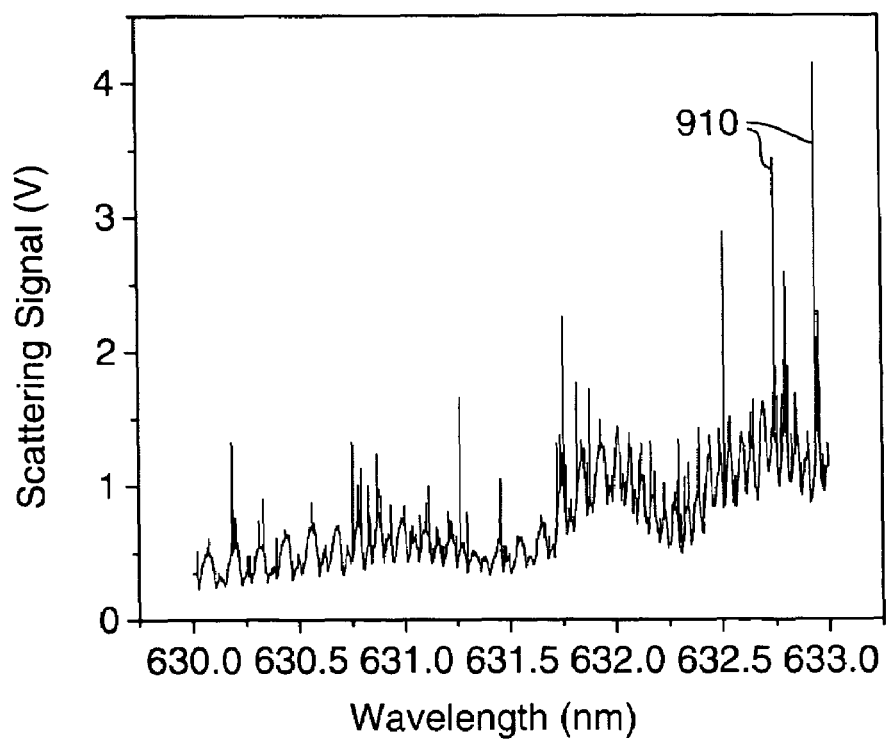

Likewise, the cylindrical resonator shows fewer resonances when the laser is scanned over the range 630 nm-633 nm (FIG. 9C) than does the bulge-like cavity (FIG. 8). In FIG. 9C, the structure detected at the level of about 0.25 V is noise, and the resonant modes show up as tall, narrow spikes 910. Again, there are fewer modes in the given wavelength range than for the bulge-like microcavity.

Figure 10:
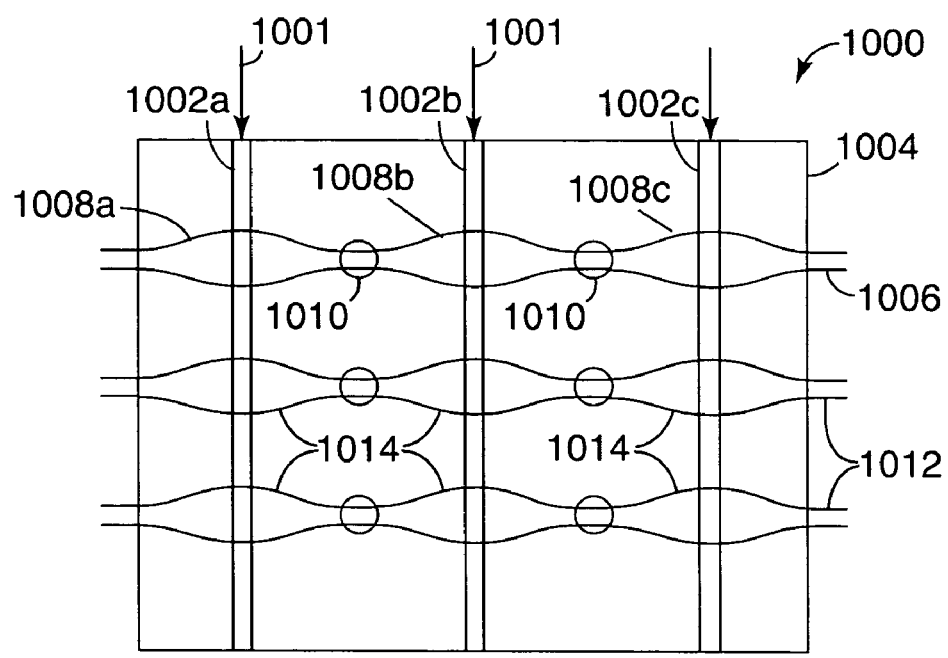
FIG. 10 schematically illustrates a microcavity array formed using bulge-like microcavities, according to principles of the present invention.

An example of a sensor array 1000, based on the use of multiple bulge-like microcavities, is schematically illustrated in FIG. 10. A number of waveguides 1002 receive light 1001 from a light source (not shown). The waveguides 1002 may be positioned on a substrate 1004. A first bulge-like cavity member 1006, carrying a number of bulge-like microcavities 1008, is positioned over the waveguides 1002. The bulge-like microcavities 1008 are spaced apart by the same spacing as the waveguides 1002, so that the different bulge-like microcavities 1008a, 1008b, 1008c optically couple to respective waveguides 1002a, 1002b and 1002c. The bulge-like cavity member 1006 may also be attached to the substrate 1004, for example, using adhesive 1010 such as Norland Optical Adhesive 61, available from Norland Products, Cranbury, N.J. Additional bulge-like cavity members 1012, comprising additional bulge-like cavities 1014, may be disposed for coupling light from the waveguides 1002 into the bulge-like cavities.

In a conventional cylindrical microresonator, the coupling of light from the waveguide to the microresonator is sensitive to the alignment between the waveguide and the microresonator: if the light is not injected into the equatorial mode of the microresonator, then the light may enter a low Q mode and be quickly lost. The coupling of light into a bulge-like cavity member 1006 is less sensitive to the alignment between the bulge-like cavities 1008 and the waveguides 1002, however, since the bulge-like cavities 1008 provide light confinement in three dimensions, and not just two as with a cylindrical microcavity. Furthermore, even though the cylindrical microcavity may have a large lateral extent, along the cylindrical axis, for example when formed from an optical fiber, the waveguide that couples light into the cylindrical microcavity is relatively narrow. Relatively wider waveguides support greater numbers of transverse modes, thus increasing the possibility that light from the waveguide will enter into a non-equatorial WGM of the cylindrical microcavity and be lost. Wider waveguides may be used with bulge-like microcavities, however, since the three dimensional confinement properties of the bulge-like microcavity permits the efficient excitation of non-equatorial modes that have a high Q. The use of wider waveguides may lead to an improved optical coupling efficiency for light between the light source and the waveguide and between the waveguide and the microcavity.

Bulge-like cavity microresonators retain many desirable optical properties, including three-dimensional light confinement and high Q-factors. As compared to a microsphere, a bulge-like cavity can be more easily mass-produced with a size and shape and aligned with a waveguide array at predefined positions. Furthermore, the use of a bulge-like cavity may lead to the use of a larger interaction surface area where there is an interaction between the light in the WGM and a fluorophore outside the microcavity. This interaction may lead to an increased effective analyte capture with a concomitant increase in sensitivity.

Rather than pulling a softened optical fiber to make a bulge-like microcavity, the bulge-like cavity may also be formed using other methods, for example molding. The material used to form the microcavity may be any suitably moldable material that also has optical properties appropriate for high Q microcavities, above 1000, for example low absorption and scattering loss. Polymers may be used as moldable materials, for example, acrylates, such as polymethyl methacrylate, polysiloxanes, such as dimethylpolysiloxane. Examples of suitable polysiloxanes include Q3-6696 UV curable polysiloxane or SYLGARD 184 available from Dow Corning, Midland, Mich., OF-206 available from Shin-Etsu, Tokyo, Japan, or GP-554 available from Genesee Polymers, Flint, Mich. Other suitable polymers include polyesters such as Vicast™, supplied by AOC, Collierville, Tenn. The use of polymers enables the fabrication of microcavities with values of Q in excess of 1000, and values of up to $5 \times 10^6$ have been reported.

Figure 11A:
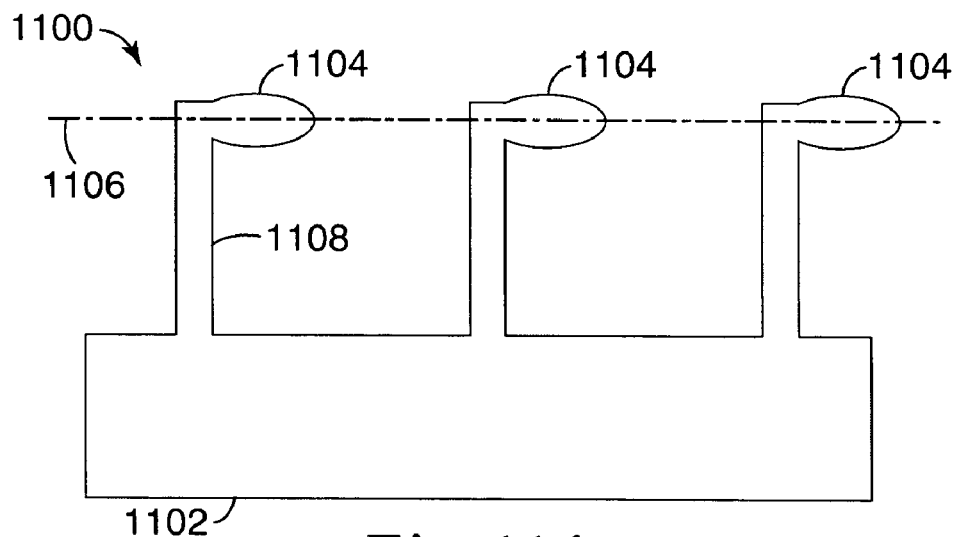
FIGS. 11A and 11B schematically illustrate bulge-like cavity members with a plurality of bulge-like cavities according to principles of the present invention.

Molded bulge-like microcavities may be provided with an attached support member for ease of handling, and a support member may support one or more different bulge-like cavities. One example of a molded set 1100 of bulge-like microcavities is schematically illustrated in FIG. 11A, which shows a support member 1102 that supports multiple bulge-like microcavities 1104 via transverse support members 1108. It will be appreciated that the use of molding techniques permits the fabrication of wide range of bulge-like microcavity shapes, and so the shapes of the bulge-like microcavities 1104 are provided for illustration only. Furthermore, the support member 1102 may be formed in different shapes and may support different numbers of bulge-like microcavities 1104. In addition, the molded set of microcavities may be used in conjunction with an array of waveguides 1002. In the illustrated embodiment, the bulge-like microcavities 1104 share a common longitudinal axis 1106, although this need not be the case and the microcavities 1104 may each have different longitudinal axes. The transverse support members 1108 extend in a direction that has a component transverse to the axis 1106.

Figure 11B:
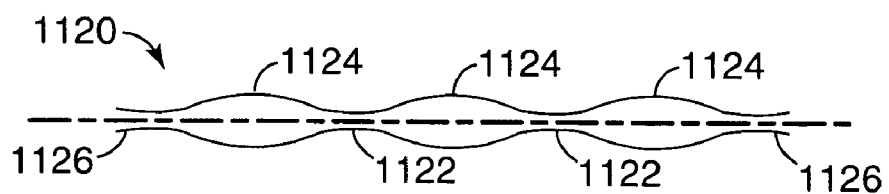

Another approach to forming polymer microcavities is to mold a continuous linear array 1120 of bulge-like microcavities 1124, for example as shown in FIG. 11B. The bulge-like microcavities 1124 are connected via connecting regions 1122. The linear array 1120 may be externally supported by a support member (not shown) attached to one or both ends 1126 of the array 1100. Such a linear array may be fabricated, for example, to be entirely formed of the moldable material.

In another approach, the bulge-like microcavity may be formed by molding a polymer outer layer that surrounds a core formed of a different material. For example, the starting material for a bulge-like microcavity may be a polymer-coated glass core, for example a silica glass core. The polymer outer layer is molded to produce the bulges that form the bulge-like cavities 1124. The WGMs may lie mainly within the polymer outer layer, or entirely within the polymer outer layer.

Accordingly, the present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. A microresonator array device, comprising:
   at least first and second optical waveguides spaced apart from each other;
   first bulge-like microcavity member formed with at least first and second bulge-like microcavities and extending across the first and second optical waveguides first bulge-like microcavity positioned proximate the first optical waveguide so as to optically couple light between the first bulge-like microcavity and the first optical waveguide and the second bulge-like microcavity positioned proximate the second optical waveguide so as to optically couple light between the second bulge-like microcavity and the second optical waveguide; and
   at least first and second optical detectors disposed to detect light associated with the first and second bulge-like microcavities respectively.

2. A device as recited in claim 1, wherein at least one the first and second optical detectors is optically coupled to receive light propagating along at least one of the first and second optical waveguides respectively.

3. A device as recited in claim 1, wherein at least one the first and second optical detectors is disposed proximate at least one of the first and second bulge-like microcavities respectively so as to detect the light, associated with the respective at least one of the first and second bulge-like microcavities, propagating through free space.

4. A device as recited in claim 1, further comprising a wavelength selective element disposed to wavelength select light propagating to at least one of the first and second optical detectors.

5. A microresonator array device, comprising:
   at least first and second optical waveguides spaced apart from each other; and
   a first budge-like microcavity member formed with at least first and second bulge-like microcavities and extending across the first and second optical waveguides, the first bulge-like microcavity positioned proximate the first optical waveguide so as to optically couple light between the first bulge-like microcavity and the first optical waveguide and the second bulge-like microcavity positioned proximate the second optical waveguide so as to optically couple light between the second bulge-like microcavity the second optical waveguide, wherein the first and second bulge-like microcavities are each elongated along a first microcavity axis.

6. A device as recited in claim 5, wherein the first bulge-like microcavity member extends in a direction having a component transverse to the first microcavity axis.

7. A microresonator array device, comprising:
   at least first and second optical waveguides spaced apart from each other; and
   a first bulge-like microcavity. member formed with at least first and second bulge-like microcavities and extending across the first and second optical waveguides, the first bulge-like microcavity positioned proximate the first optical wave guide so as to optically couple light between the first bulge-like microcavity and the first optical waveguide and the second bulge-like microcavity positioned proximate the second optical waveguide so as to optically couple light between the second bulge-like microcavity and the second optical waveguide, wherein the first bulge-like microcavity member is formed as an elongated member having a length and the first and second bulge-like microcavities are disposed at different positions along the length of the first bulge-like microcavity member.

8. A device as recited in claim 7, wherein the first bulge-like microcavity member extends in a narrowed portion between the first and second bulge-like microcavities.

9. A microresonator array device, comprising:
at least first and second optical waveguides spaced apart from each other; and
a first bulge-like microcavity member formed with at least first and second bulge-like microcavities and extending across the first and second optical waveguides, the first bulge-like microcavity positioned proximate the first optical waveguide so as to optically couple light between the first bulge-like microcavity and the first optical waveguide and the second bulge-like microcavity positioned proximate the second optical waveguide so as to optically couple light between the second bulge-like microcavity and the second optical waveguide, wherein at least one of the first and second bulge-like microcavities comprises a sidewall having a cylindrical sidewall portion.

10. A microresonator array device, comprising:
at least first and second optical waveguides spaced apart from each other;
a first bulge-like microcavity member formed with at least first and second bulge-like microcavities and across the first and second optical waveguides, the first bulge-like microcavity positioned proximate the first optical waveguide so as to optically couple light between the first bulge-like microcavity and the first optical waveguide and the second bulge-like microcavity positioned proximate the second optical waveguide so as to optically couple light between the second bulge-like microcavity and the second optical waveguide; and
at least a second bulge microcavity member formed with at least third and fourth bulge microcavities at different positions, the third bulge-like microcavity positioned proximate the first optical waveguide so as to optically couple light between the third bulge-like microcavity and the first optical waveguide and the fourth bulge-like microcavity positioned proximate the second optical waveguide so as to optically couple light between the fourth bulge-like microcavity and the second optical waveguide.

* * * * *

UNITED STATES PATENT AND TRADEMARK OFFICE
CERTIFICATE OF CORRECTION

PATENT NO. : 7,352,933 B2  Page 1 of 1
APPLICATION NO. : 10/855462
DATED : April 1, 2008
INVENTOR(S) : Xudong Fan It is certified that error appears in the above-identified patent and that said Letters Patent is hereby corrected as shown below:

Title Page (3) Col. 1 line 3
Item [56], References Cited, OTHER PUBLICATIONS, after "533-535." delete "Appl. Phys. Lett., vol. 23, No. 5, Sep. 1, 1973, pp. 237-239."

Title Page (3) Col. 2 line 8
Item [56], References Cited, OTHER PUBLICATIONS, after "Boundary"," delete "no date." and insert -- Appl. Phys. Lett., vol. 23, No. 5, Sep. 1, 1973, pp. 237-239. --, therefor.

Column 10
Line 15, In Claim 1, insert -- a -- before "first".
Line 17, In Claim 1, after "waveguides" insert -- , the --.
Line 43, In Claim 5, delete "device,comprising:" and insert -- device, comprising: --, therefor.
Line 46, In Claim 5, delete "budge" and insert -- bulge --, therefor.
Line 55, In Claim 5, after "microcavity" insert -- and --.
Line 65, In Claim 7, delete "microcavity." and insert -- microcavity --, therefor.

Column 11
Line 2, In Claim 7, delete "wave guide" and insert -- waveguide --, therefor.

Column 12
Line 8, In Claim 10, insert -- extending -- before "across".

Signed and Sealed this

Twenty-sixth Day of August, 2008

JON W. DUDAS
*Director of the United States Patent and Trademark Office*